United States Patent

Ricco et al.

[11] Patent Number: 5,820,922
[45] Date of Patent: Oct. 13, 1998

[54] METHOD FOR LOCALIZED DEPOSITION OF NOBLE METAL CATALYSTS WITH CONTROL OF MORPHOLOGY

[75] Inventors: Antonio J. Ricco; Ronald P. Manginell, both of Albuquerque, N. Mex.; Robert J. Huber, Bountiful, Utah

[73] Assignee: Sandia Corporation, Albuquerque, N. Mex.

[21] Appl. No.: 767,987

[22] Filed: Dec. 17, 1996

[51] Int. Cl.[6] ............................ C23C 16/18; C23C 16/40
[52] U.S. Cl. ................ 427/125; 427/248.1; 427/250; 427/252; 427/249; 427/255.3; 427/126.3; 502/527
[58] Field of Search .............................. 427/248.1, 250, 427/251, 252, 587, 124, 125, 249, 255.3, 126.3; 502/527; 73/31.06, 23.31

[56] References Cited

U.S. PATENT DOCUMENTS 4,096,823  6/1978  Schladitz .................................. 118/48

FOREIGN PATENT DOCUMENTS 018221  10/1980  European Pat. Off. .

*Primary Examiner*—Shrive Beck
*Assistant Examiner*—Timothy Meeks
*Attorney, Agent, or Firm*—Gregory A. Cone

[57] ABSTRACT

A combustible gas sensor that uses a resistively heated, noble metal-coated, micromachined polycrystalline Si filament to calorimetrically detect the presence and concentration of combustible gases. A thin catalytic Pt film was deposited by CVD from the precursor $Pt(acac)_2$ onto microfilaments resistively heated to approximately 500 °C.; Pt deposits only on the hot filament. The filaments tested to date are 2 $\mu$m thick ×10 $\mu$m wide ×100, 250, 500, or 1000 $\mu$m-long polycrystalline Si; some are overcoated with a 0.25 $\mu$m-thick protective CVD $Si_3N_4$ layer.

12 Claims, 10 Drawing Sheets

METHOD FOR LOCALIZED DEPOSITION
OF NOBLE METAL CATALYSTS WITH
CONTROL OF MORPHOLOGY

CROSS-REFERENCE TO RELATED APPLICATIONS

This application is related to Ser. No. 08/766,142 for a Calorimetric Gas Sensor.

STATEMENT REGARDING FEDERALLY SPONSORED RESEARCH

This invention was made with Government support under Contract DE-AC04-94AL85000 awarded by the U.S. Department of Energy. The Government has certain rights in the invention.

BACKGROUND OF THE INVENTION

This invention relates to methods for depositing noble metal catalyst materials in a localized region and with specific control of the morphology and structure of the resulting catalyst. More particularly, this invention relates to calorimetric combustible gas sensors in which a catalyst is deposited on one of a pair of filaments by a process of heating only the one filament in an atmosphere containing a gaseous compound of the catalyst such that the catalyst deposits only upon the heated filament.

Combustible gases such as methane, hydrogen, and the vapors of gasoline and other fuels pose a threat to safety when they accumulate at explosive concentrations. A relatively well developed technology for the detection of such combustible species in air is the use of a heated noble metal filament, typically Pt, the temperature of which increases when combustion occurs on its surface. A slightly more complex variation of this device is known as a "pellistor": the Pt wire is embedded in a high-surface-area ceramic pellet, which may itself contain catalytic metal particles. Such pellistors are also used for the detection of CO and the measurement of natural gas "BTU-content" in commercial systems, and have been examined in the laboratory for measuring unburned hydrocarbon emissions from automobile engines. In any of these applications, the change in filament resistance resulting from a temperature increase due to combustion of the filament or pellet surface is detected to provide an indication of the presence of the combustible species.

There is a need to miniaturize this technology, taking advantage of the potential economy of Si microfabrication technology for large numbers of devices and the feasibility of integrating control and measurement circuitry, in addition to utilizing small size as a means to significantly reduce power consumption and response time. We are utilizing surface micromachining technology, fabricating microfilaments from polycrystalline Si films, with the finished microfilaments separated from the underlying Si substrate by a gap to provide thermal isolation. Similar microfilaments have been previously explored in some detail as potential incandescent light sources and hot-wire anemometers but have as yet to be exploited for chemical sensing purposes. The filaments have some features in common with recently developed "microhotplates" made using Si microfabrication technology and applied to chemical detection but offer the potential advantage of considerably less thermal mass, with consequent reductions in power consumption and response time.

BRIEF SUMMARY OF THE INVENTION

In this invention, the catalyst is exposed to the combustible gas on one filament in each of the pairs of filaments. We have discovered that the catalyst, typically a noble metal such as Pt, can be successfully deposited upon the one filament by heating that filament in an atmosphere that contains a gaseous compound containing the catalytic substance. The gaseous compound arises from a solid catalyst precursor that is heated to a lower temperature in a chamber that encloses the filament. The catalyst deposits only upon the properly heated surface of the filament. Since this deposition is done after the rest of the combustible gas sensor has been fabricated, there is no danger of contaminating the earlier process steps and no risk of overheating the remainder of the sensor since only the one filament is heated.

DETAILED DESCRIPTION OF THE INVENTION

Figure 1A:
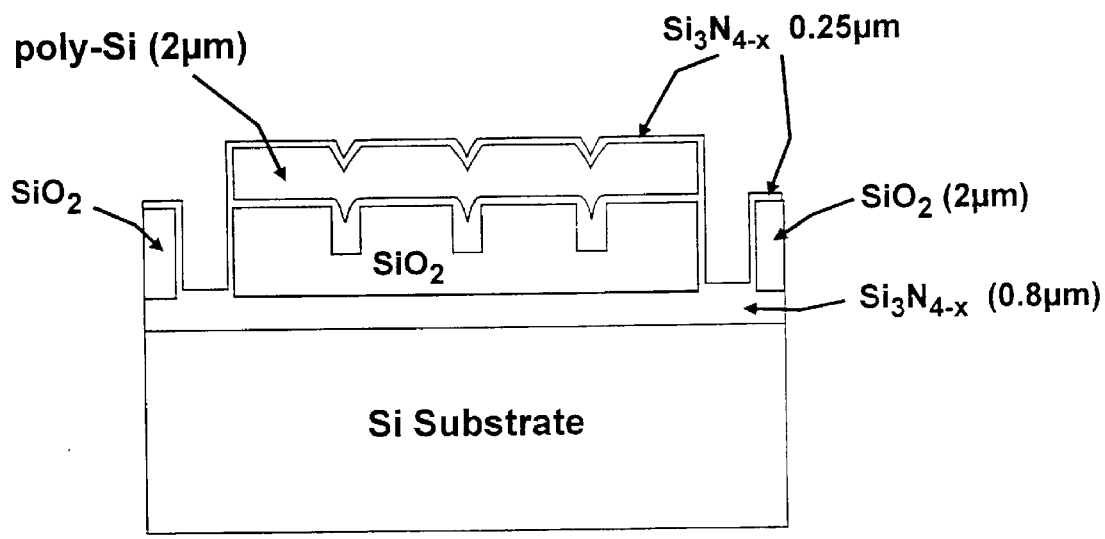
FIG. 1A is a side cross sectional view of one poly-silicon filament prior to release from the substrate displaying the long axis of the filament.
Figure 1B:
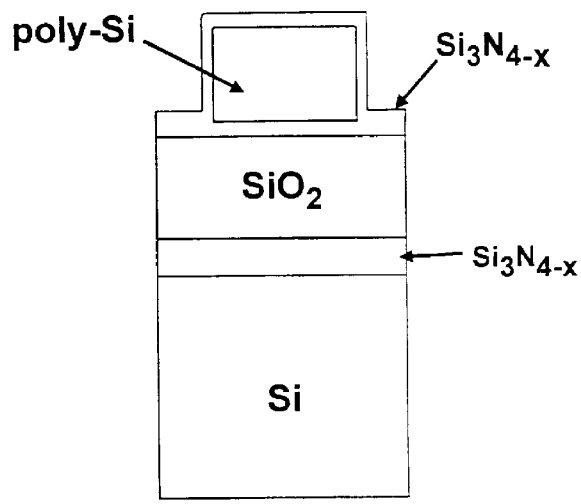
FIG. 1B is cross sectional view of the filament of FIG. 1A with the section taken across the middle of the filament.

One preferred embodiment for this invention includes a 0.25 $\mu$m CVD $Si_3N_4$ overlayer to protect the poly-Si filaments from long-term thermal oxidation, which would occur at the elevated temperatures required for the detection of some combustible species; FIGS. 1a and 1b show side and cross sectional schematic views respectively of the microfabricated poly-Si filament. The process of forming the poly-Si filaments is as follows. (1) Deposit 0.8 $\mu$lm low-stress $Si_3N_4$ 8500° C., 4:1 $SiH_2Cl_2NH_3$, stress about 100 MPa tensile. (2) Deposit 2 $\mu$m $SiO_2$ from $Si(OEt)_4$. (3) Pattern and plasma etch dimples, about 1 $\mu$m into the $SiO_2$ to prevent adhesion of filaments to the Si substrate. (4) Pattern and plasma etch anchor holes through the $SiO_2$. (5) Deposit 0.25 $\mu$m $Si_3N_4$ to protect filament bottom. (6) Deposit 2 $\mu$m in-situ P-doped poly-Si. (7) Anneal at 11000° C. for 3 hours. (8) Pattern and plasma etch poly-Si to form filaments. (9) Deposit 0.25 $\mu$m $Si_3N_4$ to protect filament top and sides. (10) Release the poly-Si filaments from the Si substrate by dissolving the $SiO_2$ in 1:1 HF:HCl for 30 minutes. This final step creates the airgap between the filament and the substrate that is critical to achieving the low thermal mass. Care must be taken in subsequent processing steps for catalyst deposition to ensure that the gap is maintained.

Note that the nitride layer prevents the electrical conductivity of the catalytic metal overlayer (see below) from affecting control and measurement of the filament resistance/temperature, in addition to preventing metal silicide formation. We have briefly investigated one alternative to the use of poly-Si, namely "SOI" (silicon-on-insulator) technology, chiefly because single-crystal silicon filaments should demonstrate improved long-term, high-temperature stability due to the lack of grain boundaries (compared to poly-Si). Filaments can also be fabricated directly from noble metals (e.g., Pt) as an alternative to poly-Si with a noble metal external layers.

Figure 2:
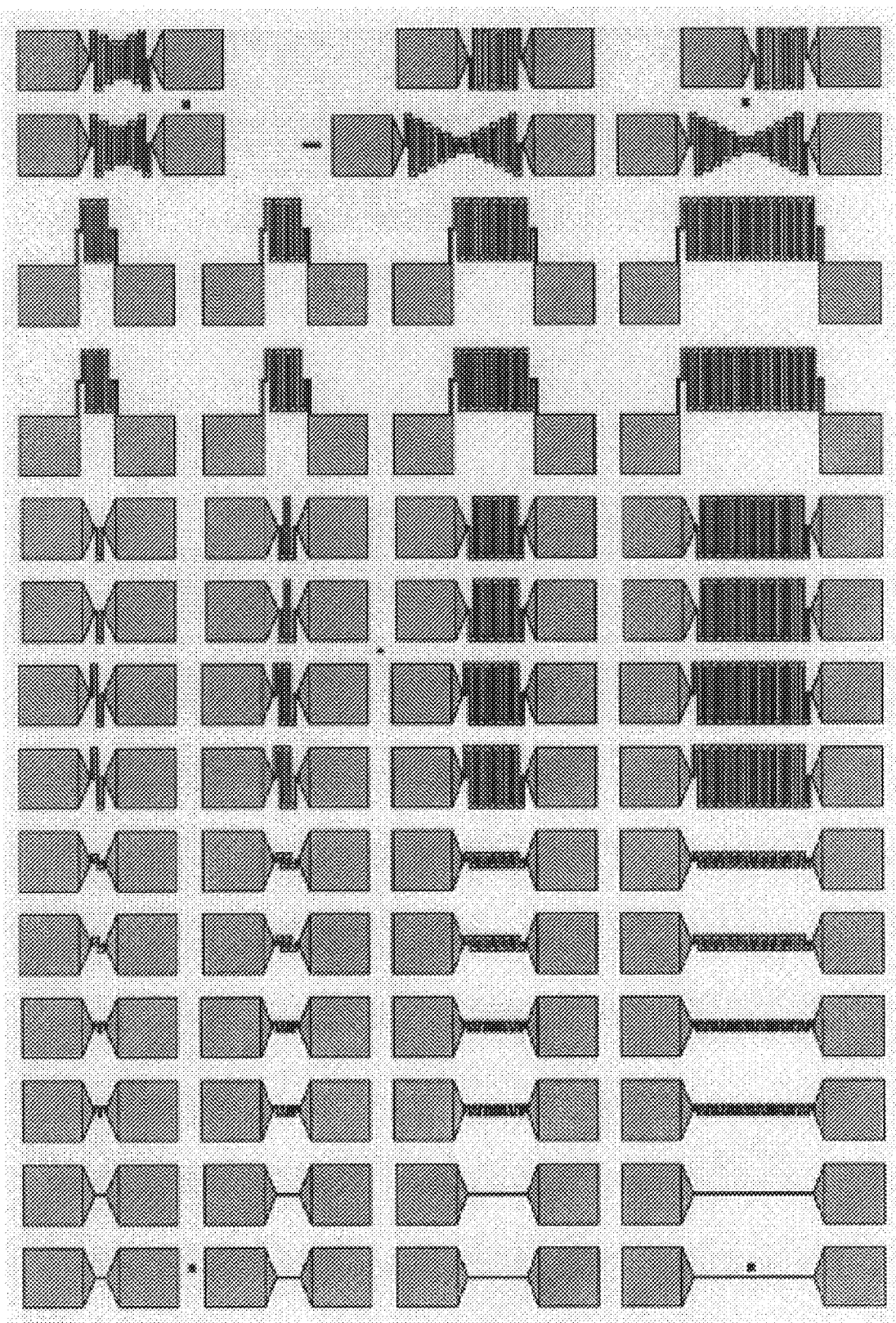
FIG. 2 is a top view of a wafer onto which have been formed a multiplicity of different configurations of the pairs of filaments with those in the bottom two rows being straight filaments of different widths and lengths and with the remainder being various different serpentine filament configurations.
Figure 3:
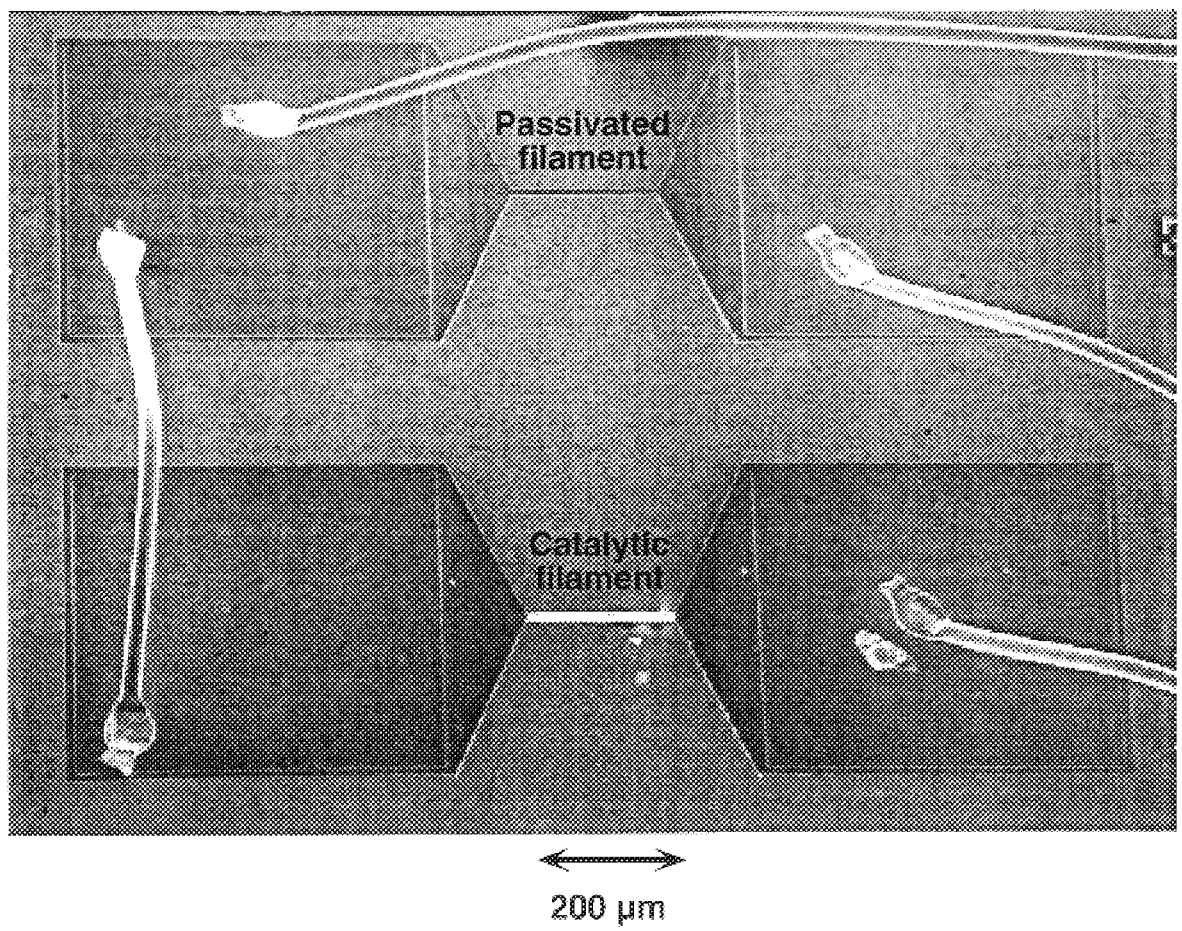
FIG. 3 is a microphotograph of one pair of filaments including the attached electrode bonding pads with the bottom filament presenting the catalyst.

A range of different filament geometries is possible. FIG. 2 shows several possibilities that have been fabricated including simple straight filaments and different serpentine configurations. They attempt to deal with problems such as buckling of the filament as a result of thermally induced stress, as well as the nonuniform temperature distribution which results from thermal conduction out the ends of the filament being the predominant mechanism for heat loss. The filaments tested for CVD and gas detection to date are 2 $\mu$m thick ×10 $\mu$m wide ×100, 250, 500, or 1000 $\mu$m-long straight geometries. While buckling has not been problematic at the moderate temperatures (300–500° C.) used for Pt CVD and for $H_2$ detection, serpentine geometries may be needed at higher temperatures. FIG. 3 shows a pair of straight 200 $\mu$m-long filaments, one bearing the additional Pt coating and the other one "bare," nitride-passivated poly-Si.

Figure 4:
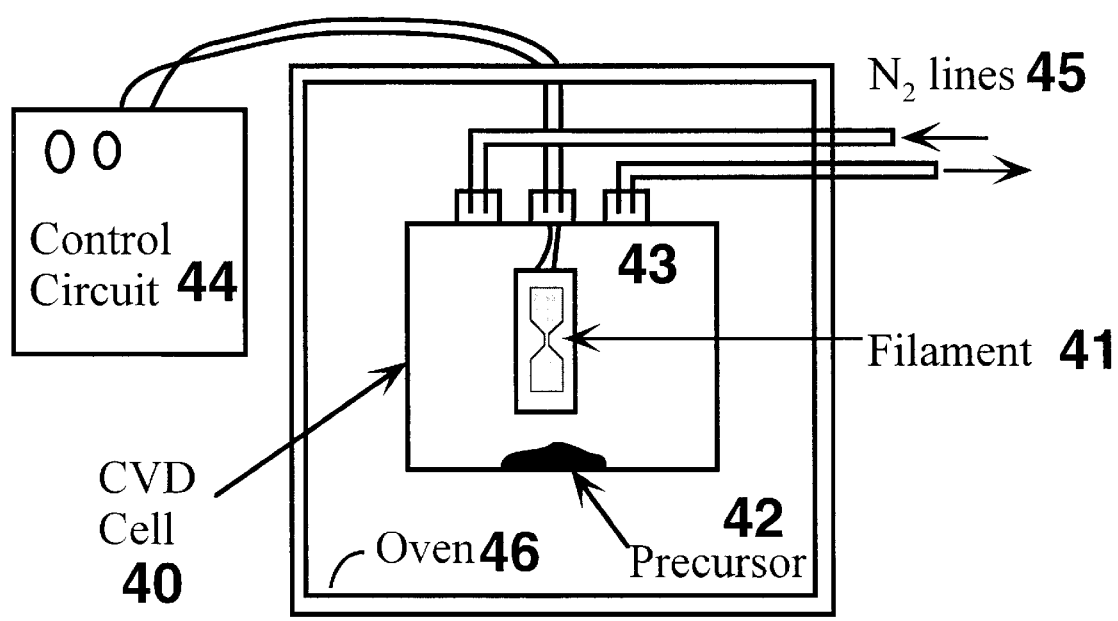
FIG. 4 is a schematic diagram of the deposition system for emplacing the catalyst onto one of the filaments in a pair.

To catalyze the combustion process on poly-Si or other non-catalytic filaments, a thin film of noble metal is deposited using "microCVD": one or more selected filaments are heated resistively (in this particular case, to approximately 500° C.) in an inert gaseous ambient that includes a volatile organometallic precursor for the desired noble metal. $Pt(acac)_2$ has been utilized herein as the precursor, but many other suitable compounds are available as well. Metal deposition occurs only on the heated filament(s), allowing different metals and/or different film thicknesses to be deposited on each filament. The simple apparatus used to accomplish this micro-CVD process is represented by FIG. 4. A teflon CVD Cell 40 houses the filament and a small amount of the catalyst precursor 42. The cell is equipped with electrical access 43 to provide power to those elements selected for catalyst deposition. The power is supplied by the control circuit 44 that raises the temperature of the selected filaments to the proper level. Nitrogen lines 45 provide an inert ambient within the cell. To vaporize the precursor, the cell is placed into an oven 46 at 1400° C. This temperature provides adequate vapor pressure of the Pt precursor used here in the cell, but no deposition occurs except on those filaments that are electrically heated by the external control circuit. Deposition of Pt is optimized for this embodiment where the filament temperature exceeds about 4500° C.

Figure 5A:
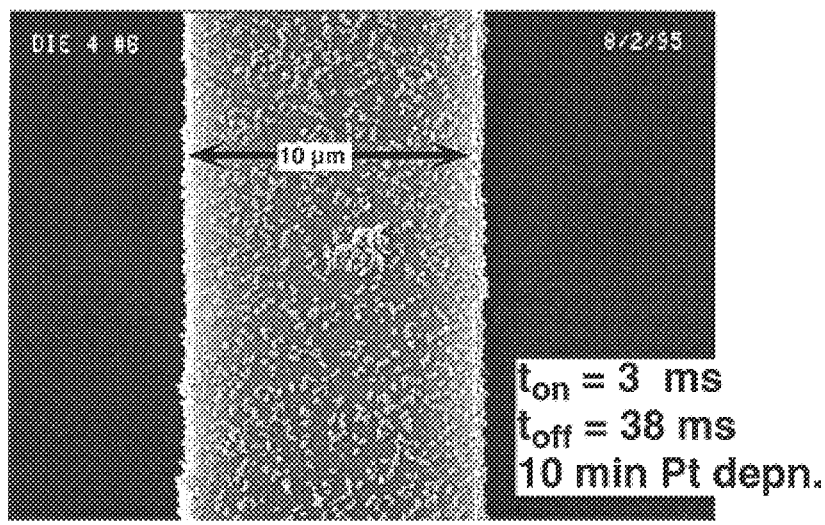
FIGS. 5A, 5B, and 5C are three microphotographs of different Pt plated filaments for which the conditions of deposition have been varied.
Figure 5B:
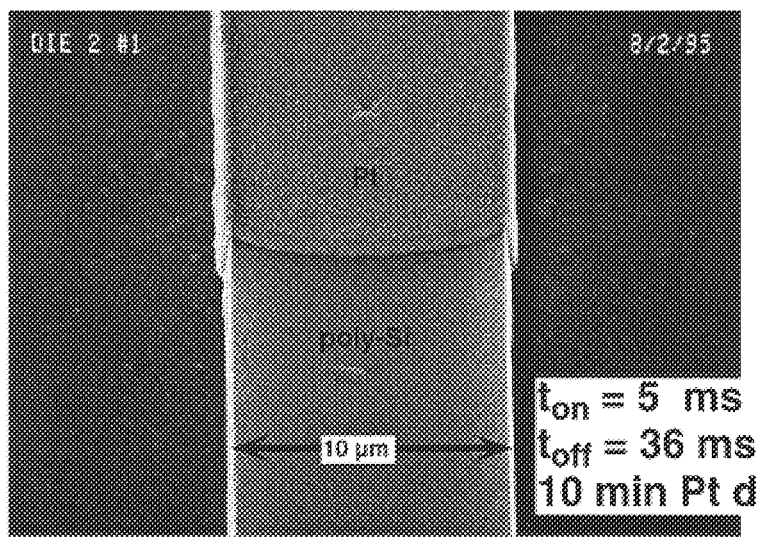
Figure 5C:
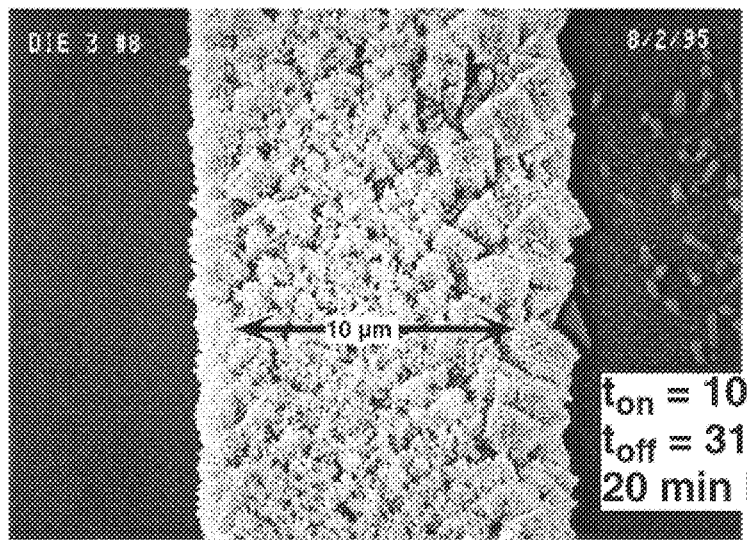
Figure 9A:
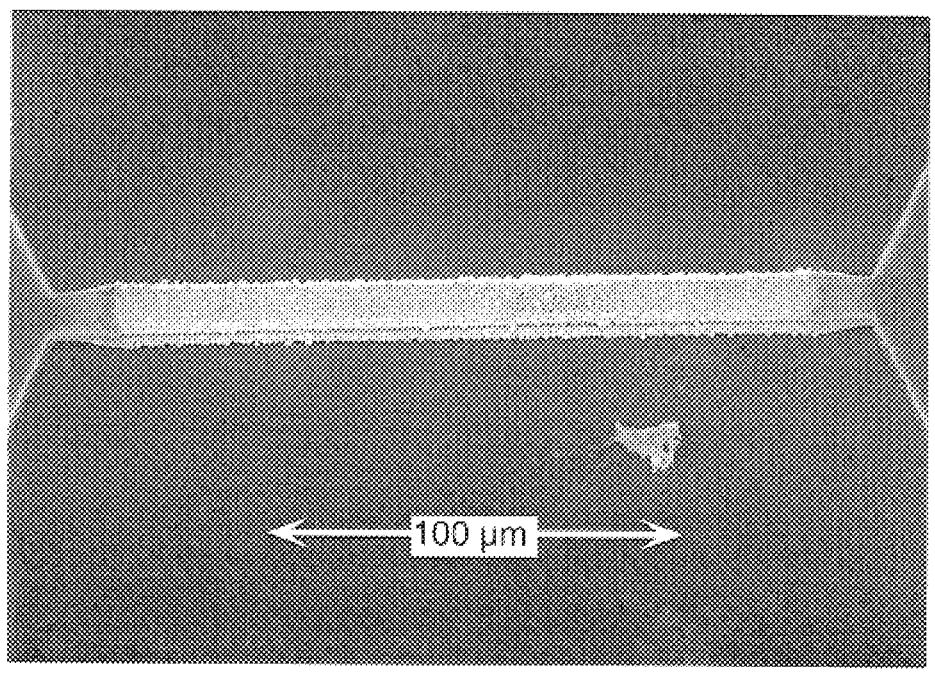
FIGS. 9A and 9B are two microphotographs of another Pt-coated filament wherein the Pt was continuously deposited as opposed to pulsed deposition as in the filaments shown in FIGS. 5A–5C.
Figure 9B:
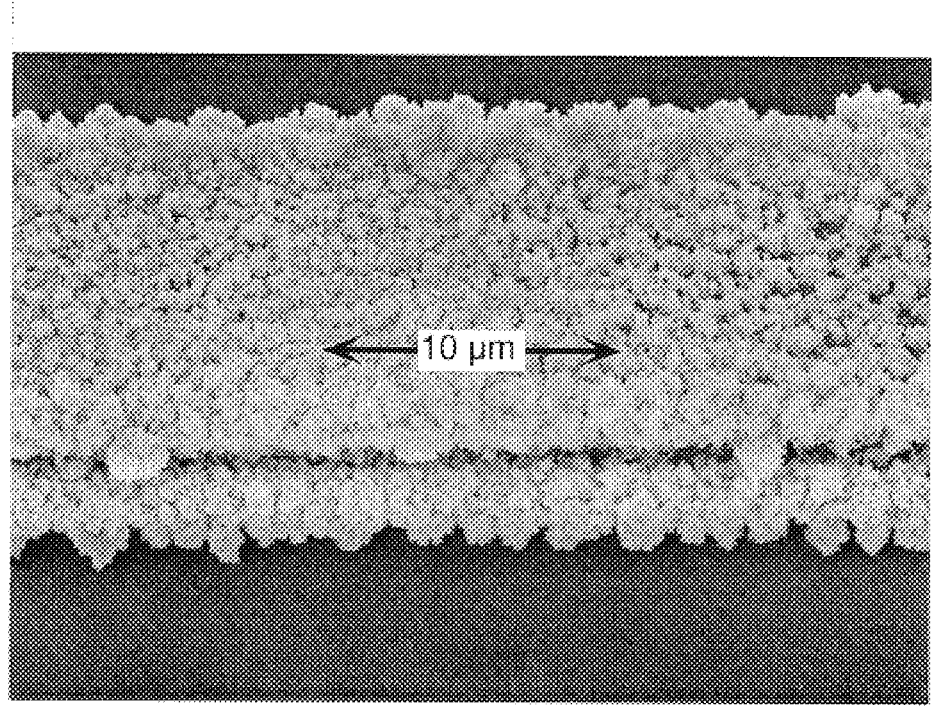

Significant advantages of this method of conferring catalytic properties to a microfilament include (1) the fact that the catalyst is deposited on (and only on) one or more electrically selected filaments; (2) the process occurs post-packaging, so there is no possibility of conflict due to process or materials incompatibilities with the Si microfabrication process; (3) a wide variety of metals (e.g., Pt, Pd, Rh, Ir, Ru, Re, Ni, Au), ceramic materials (e.g., $TiO_2$, $SnO_2$, $ZrO_2$, $SrTiO_3$, SiC, etc.), as well as mixtures of the metals and/or the ceramics, can be deposited using this technique, and the formation of alloys and/or layered films using a mixture of precursors and/or sequential deposition from different precursors is feasible as well; (4) we have discovered that control of the filament temperature, the total time of deposition, and particularly the nature of the duty cycle (ratio of "on time" to "off time", as well as the absolute values of the on time and off time), during catalyst deposition provides a means to control the morphology and microstructure of the catalyst layer. The morphological variety obtainable and the conditions that produce some of the various microstructures are typified by the results presented in FIGS. 5A, 5B and 5C. In FIG. 5A, the heated pulse is ON for 3 ms and OFF for 38 ms for a total of 10 minutes. The Pt appears as discrete bumps on the poly-Si filament. In FIG. 5B, the heat pulse is ON for 5 ms and OFF for 36 ms for a total of 10 minutes. Notice the smooth continuous coverage under these conditions. Also of interest here is the terminal edge of the catalyst. The temperature profile on a filament is parabolic with the highest temperature in the middle of the filament. As one approaches the ends of the filament, the temperature decreases due to conduction of heat to the thermally massive substrate. This view shows the position where the temperature dropped below that necessary to support deposition near one of the ends of the filament. In FIG. 5C the heat pulse is ON for 10 ms and OFF for 31 ms for a total of 20 minutes. Here identifiable Pt crystals have formed. Although the surface area of the catalyst has increased here, there is also a risk that one of the crystals might extend down to touch the substrate which could adversely change the thermal mass characteristic of the filament and its response. FIG. 9 shows the results of continuous wave (CW) heating for 20 minutes with even greater Pt deposition than is present in FIG. 5C.

There are two important aspects to the effective operation of the catalytic microfilament gas sensor: (1) the use of a feedback-based control circuit to keep the microfilament at a constant temperature at all times, regardless of changes in ambient conditions or concentrations of combustible species; (2) measurement based on the use of a differential pair of filaments, one of which bears a catalytic coating to facilitate surface combustion of the species to be detected, the other passivated so that no combustion occurs on its surface. The circuit we use to control the microfilament maintains a constant (average) temperature by adjusting the supplied current to keep the total filament resistance at a constant value (temperature and resistance are directly related to one another). There are two main reasons for operating both the sensing filament and its passivated reference filament at the same, constant temperature. First, variations in ambient conditions, including but not limited to gas flow rate, gas thermal conductivity, temperature, and relative humidity affect the rate of heat loss of both the sensing and reference filaments in precisely the same manner, so that the changes in input power to the sensing and reference filaments that occur as a consequence of such ambient variations will be equal and therefore cancel one another when the two filaments are operated in a differential mode. Second, identical thermal histories increases the likelihood that any gradual changes in the characteristics of the sensing microfilament (e.g., changes in resistivity due to electrothermally induced dopant migration) will be mirrored in the reference microfilament, and therefore cancel. With operation in this differential mode, a sensor signal results only if combustion occurs on the catalytic microfilament, in which case the input power decreases in relation to the concentration of combustible species; no such similar input power decrease is recorded for the passivated (noncatalytic) reference filament.

Figure 6:
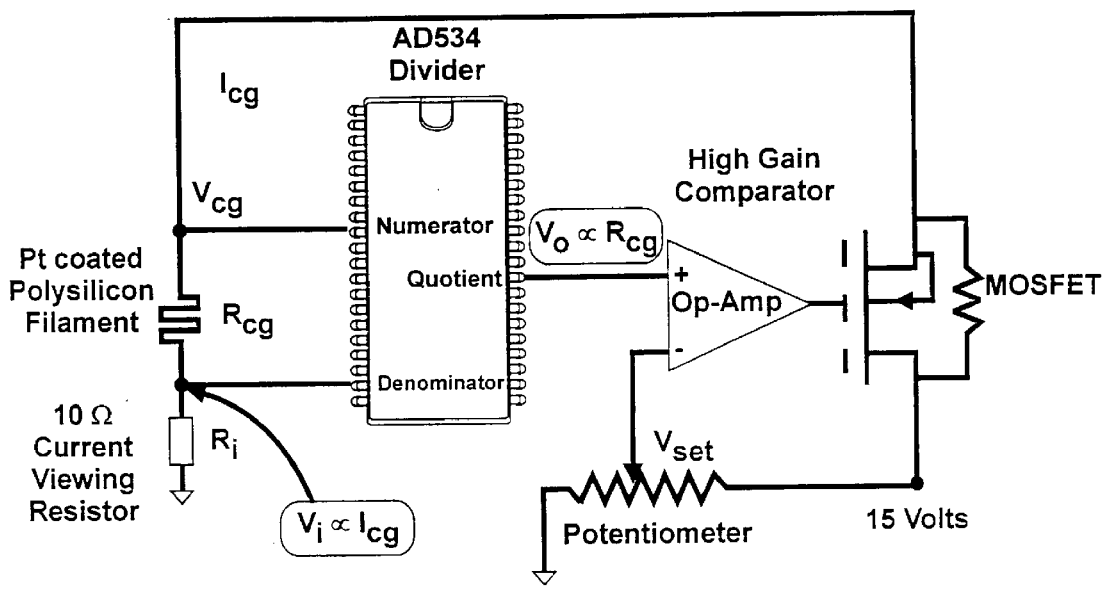
FIG. 6 if a schematic diagram of the control circuit for heating the filaments that maintains constant temperature in the filaments and provides a measurement of the power used to do so.

The control circuit is illustrated in FIG. 6. The AD 534 divider chip divides the voltage drop ($V_{cg}$) across the combustible gas sensing filament ($R_{cg}$) by voltage drop ($V_i$) across the 10 Ω current viewing resistor ($R_i$). The AD534 output voltage signal ($V_o$) is proportional to $R_{cg}$. The op-amp turns on MOSFET transistor when $V_{set}$ is greater than $V_o$. The MOSFET current ($I_{cg}$) heats the filament and ($R_{cg}$) stablilizes at the resistance value that is set by the potentiometer. Monitoring $V_i$ gives the change in power required to maintain $R_{cf}$ at the set point.

A single catalytic/passivated microfilament pair has no inherent chemical selectivity: any combustible gas mixture, whether it is methane and oxygen, a mixture of unburned hydrocarbons in automobile exhaust, nitrous oxide and acetylene, or carbon monoxide in room air, will provide a response signal if the heat input due to its combustion on the surface of the catalytic filament (operated by the feedback circuit) provides enough change of the input power to exceed the typical noise level of the measurement system. There are, however, at least two means by which chemical selectivity can be conferred to this sensor. The first is control of the temperature of the filament. In general, every combustible species has a unique profile for its rate of combustion as a function of the temperature of the catalytic surface upon which it burns. Thus, by making measurements at several different filament temperatures (with both the sensing and reference filament programmed to step in synchronization to each temperature for a defined time period, during which a measurement of differential heat input is made), a distinct pattern of combustion rate vs. temperature can be obtained, this pattern providing a "signature" for a particular combustible species or mixture. The second parameter that affects sensitivity is the choice of catalyst on the microfilament surface. As described above, many different metals, alloys, and even multilayer metal films can be deposited on each of several different filaments. Rather than a single differential pair of filaments, there are now n differential pairs, the sensing filament of each pair coated with a different catalyst layer (it may be possible to reduce the complexity of such a system by utilizing a single reference filament for a number of different catalytic filaments, provided all are operated at the same temperature). The pattern of differential heat inputs to this array of different catalytic microfilaments will provide a signature for the particular compound or mixture of compounds. A logical extension is to combine the two methods of obtaining selectivity, thus operating each member of an array of differently coated catalytic filaments at each of several different temperatures (doing this in synchronization would allow the use of a common reference filament). The resulting multidimensional response would consist of a pattern of differential heat inputs, both as a function of temperature and of catalyst material. Such patterns are amenable to pattern recognition using any of many different techniques, such as neural networks, the Visually Empirical Region of Influence (VERI) cluster analysis developed at Sandia National Laboratories, or any of the many different mathematical techniques classified under the general heading of "chemometrics."

Figure 7:
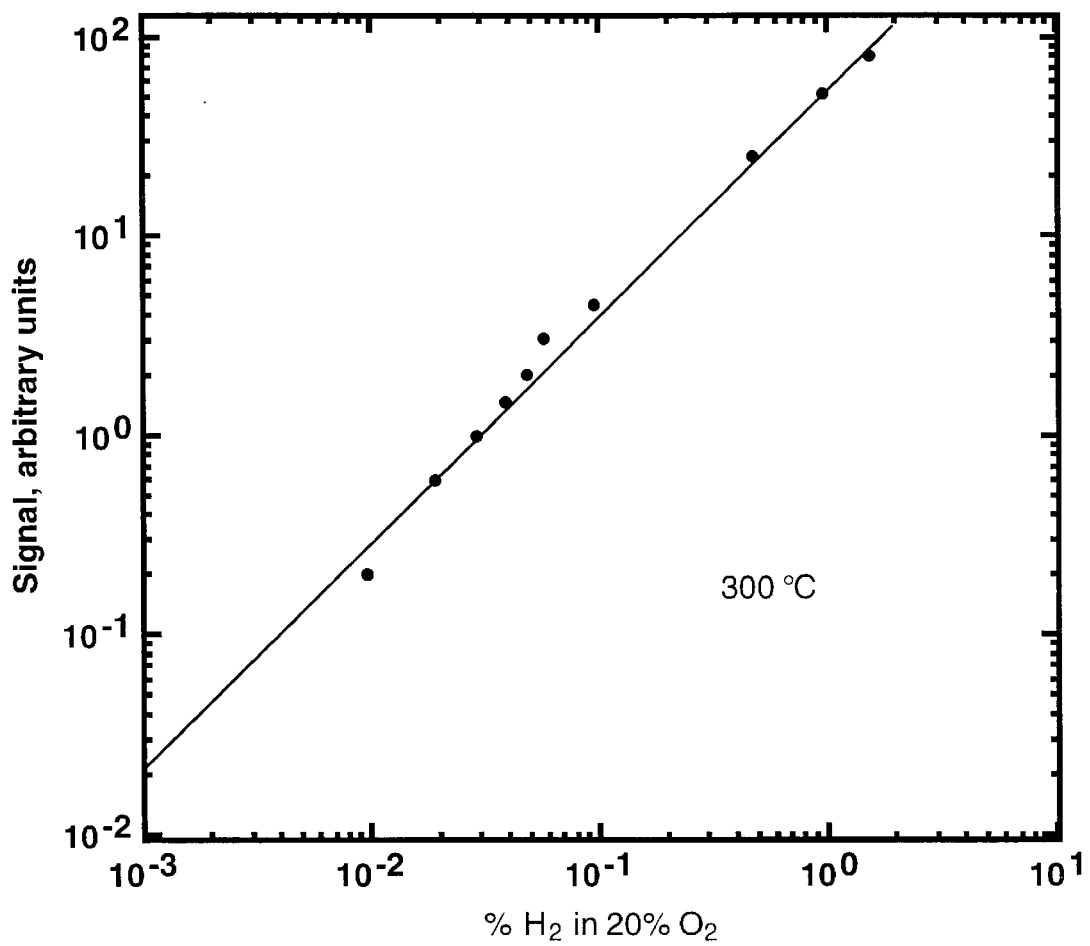
FIG. 7 is a graph showing the response of a Pt-coated filament to different hydrogen gas concentrations.

The control circuit, a schematic for which is shown in FIG. 6, was designed, built, and used successfully for the CVD of Pt onto a number of individual filaments and also for testing in combustible $H_2/O_2$ and other combustible mixtures. Using the feedback control circuit, Pt-coated filaments operating at ca. 300 ° C. (35 mW input power) were found to respond approximately linearly, in terms of the change in supply current required to maintain constant filament resistance (temperature), to $H_2$ concentrations between 100 ppm and 1% by volume in an 80/20 $N_2/O_2$ mixture. FIG. 7 shows this response on a log/log scale to accommodate the relatively wide concentration range; the slope of the best-fit line through these data is 1.1.

Figure 8:
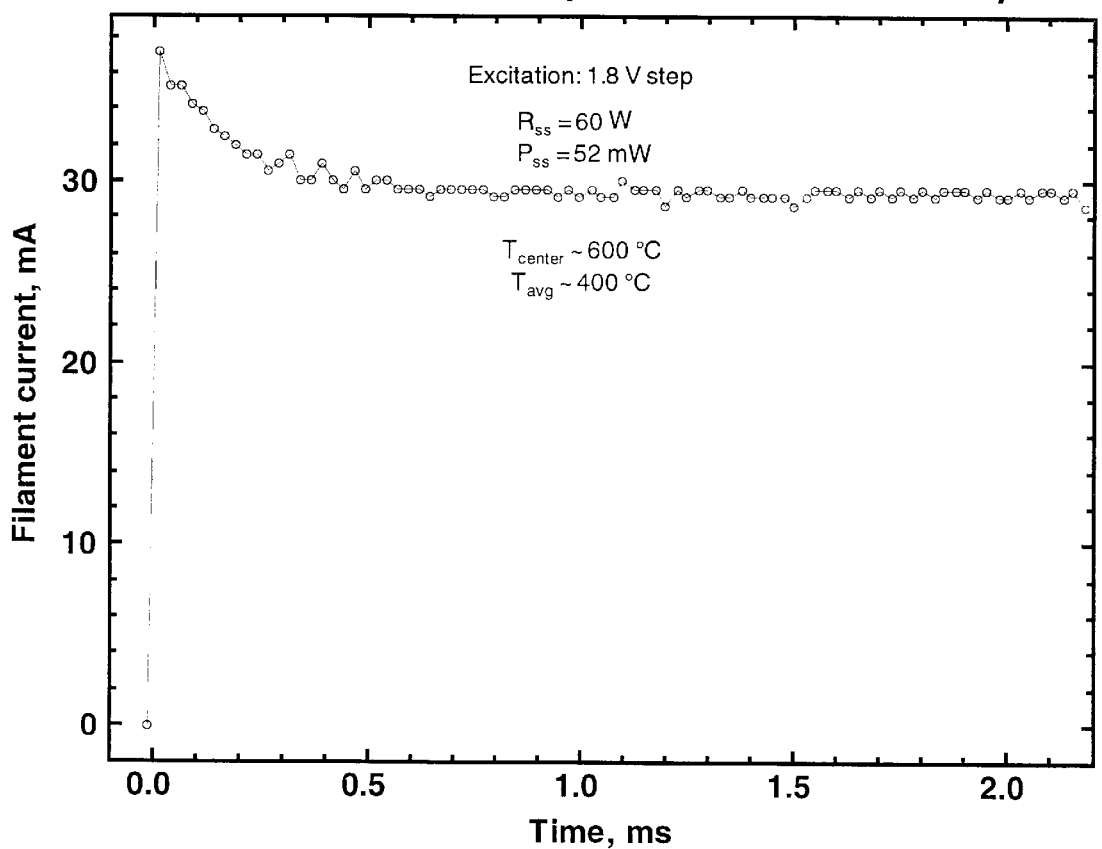
FIG. 8 is a graph showing the response time of a filament.
Figure 10:
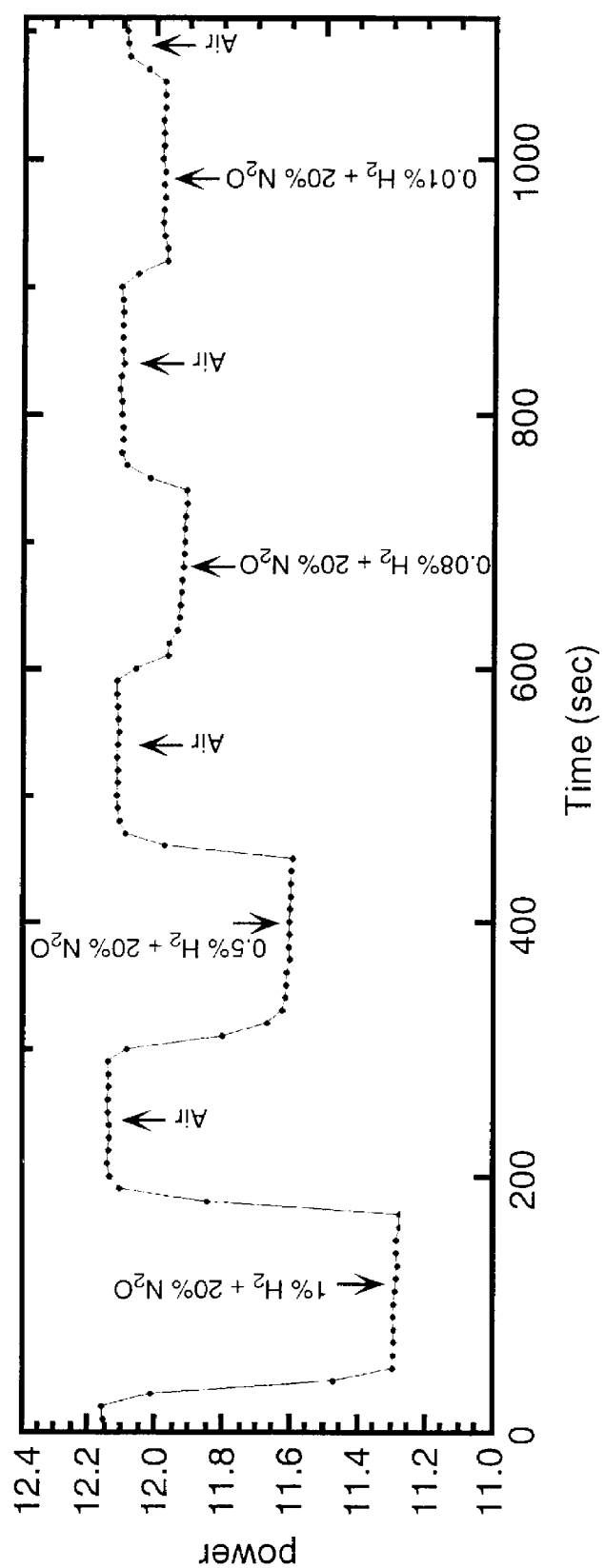
FIG. 10 is a graph showing the response of the sensor to alternating pulses of air and $H_2/N_2O$ mixtures.

An added benefit of the very low thermal mass of the microfilaments is rapid response time. The measured response time for the imposition of a current step that raises the temperature of the filament several hundred degrees above ambient is about 200 $\mu s$, as shown in FIG. 8. FIG. 10 is another graph showing the response of the sensor to alternating pulses of air and $H_2/N_2O$ mixtures.

We claim:

1. A method of depositing a catalyst on a filament in a sensor for a combustible gas comprising:

forming a first filament and a second filament on a substrate, said first and second filaments possessing the same electrical resistance-temperature characteristic; and subject said substrate having first and second filaments formed there on to an atmosphere containing a gaseous compound of the catalyst while controllably heating only the first filament thereby depositing the catalyst only upon the first filament.

2. The method of claim 1 wherein the filaments are formed so as to be disposed above and parallel to a semiconductor substrate with an airgap between the filaments and the top of the substrate.

3. The method of claim 2 wherein the filaments are supported at each end by pillars that are formed to extend upwardly from the substrate.

4. The method of claim 1 wherein the first and second filaments are formed with a core of conductive poly-silicon surrounded by a protective shell of $Si_3N_4$.

5. The method of claim 1 wherein the catalyst is selected from the group consisting of the noble metals and combinations thereof.

6. The method of claim 5 wherein the catalyst is Pt and the gaseous compound is $Pt(acac)_2$.

7. The method of claim 1 wherein the catalyst is selected from the group consisting of catalytic ceramic materials.

8. The method of claim 7 wherein the catalyst is selected from the group consisting of $TiO_2$, $SnO_2$, $ZrO_2$, $SrTiO_3$, SiC and combinations thereof.

9. The method of claim 1 wherein the step of controllably heating the first filament comprises resistively heating the first filament with pulses of power of controlled duration to a temperature above the deposition temperature for the catalyst for a first period of time.

10. The method of claim 1 wherein the step of controllably heating the first filament comprises continuously resistively heating the first filament to a temperature above the deposition temperature for the catalyst for a period of time.

11. A method of depositing a noble metal catalyst upon a microfilament comprising resistively heating the microfilament with pulses of power of controlled duration in an atmosphere containing a gaseous compound of the noble metal catalyst to a temperature above the deposition temperature for the catalyst for a first period of time to achieve a desired morphology of the deposited catalyst.

12. The method of claim 11 wherein the gaseous compound is created by heating a solid precursor to the gaseous compound at a temperature below the deposition temperature for the catalyst.

* * * * *